United States Patent [19]  [11] 4,150,151
Pader et al.  [45] Apr. 17, 1979

[54] MOUTHWASH

[75] Inventors: Morton Pader, Teaneck; Craig T. Elton, North Bergen, both of N.J.

[73] Assignee: Lever Brothers Company, New York, N.Y.

[21] Appl. No.: 859,632

[22] Filed: Dec. 12, 1977

[51] Int. Cl.² ............................................. A61K 7/16
[52] U.S. Cl. ...................................... 424/56; 424/49
[58] Field of Search ..................................... 424/49–58

[56]  References Cited

U.S. PATENT DOCUMENTS

| | | | |
|---|---|---|---|
| 2,054,742 | 9/1936 | Elbel | 424/56 X |
| 2,359,291 | 10/1944 | Gluesenkamp et al. | 424/56 X |
| 2,380,011 | 7/1945 | Baker et al. | 424/56 X |
| 2,812,284 | 11/1957 | Sanders | 424/56 |
| 3,256,155 | 6/1966 | Cahn et al. | 424/56 |
| 3,462,525 | 8/1969 | Levinsky et al. | 424/56 |
| 3,531,564 | 9/1970 | Bouchal et al. | 424/56 |
| 3,692,894 | 9/1972 | Amo et al. | 424/56 |

FOREIGN PATENT DOCUMENTS

| | | | |
|---|---|---|---|
| 975623 | 4/1962 | Fed. Rep. of Germany | 424/56 |
| 2442825 | 3/1975 | Fed. Rep. of Germany | 424/56 |
| 399917 | 10/1933 | United Kingdom | 424/56 |

OTHER PUBLICATIONS

A.D.A. Accepted Dental Therapeutics, 35th Ed. (1973), pp. 253–257, 261–265, 270–273.
Balsam et al., Cosmetics Science & Technology, 2nd Ed. (1972), vol. 1, Wiley-Interscience, N.Y., N.Y., pp. 455–457, 484–489, 494–497, 508–509, 533–536, 540, 545–549, 558.

*Primary Examiner*—Shep K. Rose
*Attorney, Agent, or Firm*—Michael J. Kelly; James J. Farrell; Melvin H. Kurtz

[57]  ABSTRACT

A physiologically acceptable, germicide free antibacterial liquid mouthwash and methods for its use is disclosed. The mouthwash comprises water, ethanol, an essential oil flavor mixture and about 0.1 to about 0.6 percent of an alkyl sulfate anionic surfactant mixture of $C_{12}$ and $C_{14}$ sulfates wherein the ratio of $C_{12}$ to $C_{14}$ alkyl sulfates is in the range of about 75:1 to about 1:1. Additional ingredients which may be incorporated within specific ranges include nonionic emulsifiers, humectants, alkali metal halides, buffering salts, sweetening agents and colorants.

54 Claims, No Drawings

MOUTHWASH

BACKGROUND OF THE INVENTION

Mouthwashes are liquid preparations specifically designed to cleanse and refresh the mouth. While many early mouthwashes comprised no more than pleasantly flavored colored solutions having limited actual efficacy over the implied coverup of oral mal odor suggested by the persistence in the mouth of residual flavor components, consumer demand has resulted in the evolution of a new generation of rinses containing specific ingredients employed therein to provide efficacious action against problems associated in the oral cavity such as, for example, mal odor, caries, gum disorders and infections.

There is a wide latitude in the choice of conventional mouthwash ingredients and components depending upon the ultimate end purpose sought from the preparation. This end purpose serves as a basis of classifying various mouthwashes into specific categories.

There appears to be six basic categories of mouthwashes: cosmetic, astringent, buffered, deodorizing, therapeutic and antibacterial.

Cosmetic mouthwashes usually contain water, alcohol, flavor and color. They may also contain nonionic surface-active agents for the purpose of assisting in the solubilization of certain flavor components as well as aiding in the irrigation and cleansing of the mouth and teeth. Cosmetic mouthwashes have had excellent consumer acceptance as these "flavored water" formulations can be made quite attractive and very pleasant to taste.

Astringent mouthwashes provide a direct effect on the oral mucosa and also provide a means for flocculating and precipitating proteinaceous material so that it may be more readily removed by flushing. These mouthwashes by their very nature of being astringent present problems in flavoring and consumer acceptance.

Buffered mouthwashes may be helpful in reducing stringy saliva or reducing mucinous deposits by dispersion of protein based on the pH of the rinse. Critical pH values, however, can result in incompatability of ingredients and severe flavor problems.

Deodorizing mouthwashes heavily depend upon perfume to mask mal odor; however, some depend upon antibacterial or other mechanisms, unrelated to such action, for their effect. Those products employing antibacterial agents suffer from the aforementioned flavoring problems.

Therapeutic mouthwashes are formulated for the purpose of relieving infection, preventing dental caries, or mitigating some other pathological condition that may be associated with the mouth, teeth or throat. The nature of the therapeutic actives, their incompatibility with other ingredients in the rinse or for that matter synergistic effects resulting in questionable combinations present severe formulation problems in the more complex systems.

Finally, antibacterial mouthwashes, i.e. mouthwashes which are efficacious against bacteria found in the mouth, which is the primary subject matter of the instant invention, have the primary purpose of reducing or removing bacteria that are usually present in large numbers in the oral cavity. Microbial populations in the mouth arise quite naturally, for example, from dental plaque, decaying food particles and from salivary stagnation. In many instances these microbes are responsible either directly or indirectly for mal odor. Additionally, these microbes can present a source of infection and are believed by some investigators to be related at least in part to such problems as caries and periodontal disease.

A full treatment of mouthwash history and technology is presented by Rosenthal in Balsam et al. *Cosmetics Science and Technology,* John Wiley and Sons, 2nd. edition, 1972, Chapter 14 inclusive, which is incorporated herein by reference.

It is well known that some of the mal odorous elements of mouth aroma are generated by bacteria. It has been suggested that the germicidal agents commonly used in mouthwashes (quaternary ammonium compounds, phenolic compounds and sometimes flavor components having germicidal action) exert their effect by destroying or inhibiting oral bacteria. However, some have proposed that the antibacterial agents can exert a deodorizing effect on the oral cavity by a mechanism which is not related to their antibacterial activity. Rosenthal supra. There is evidence in the literature that antibacterial mouthwashes are more effective than would be expected from simple action of the flavor components of those mouthwashes; antibacterial activity probably therefore must be of some importance under certain circumstances, and direct deodorization by the antibacterial agent could also be involved, e.g. quaternary ammonium compounds could interact with aroma-producing chemicals in the mouth and thereby suppress them. Additionally, flavor undoubtedly plays a role in mouthwash activity,. While some flavors do have antimicrobial properties, and while it has been reported that mouthwashes comprising nothing more than flavored water can, to a limited extent, combat mouth aromas, such action is too minimal for a truly efficaceous product. It is more likely, however, that the major role of the flavor probably is simply to attempt to mask undesirable mal odors emanating from the mouth.

Attempts to improve efficacy against oral mal odor and other oral problems recently has resulted in increased stress on the importance of bacterial effectiveness. The compounds, however, that seem to demonstrate efficacy, at least at levels where bactericidal activity can be demonstrated, contribute significantly to flavor, foam, clarity and irritancy problems. Lacking physiological acceptance, these products have proved unacceptable to many consumers for a number of reasons. Examples of antibacterial agents employed in mouthwashes include phenolic compounds such as beta naphthol, thymol, carvacrol, chlorothymol, amyl-, hexyl-, heptyl and octylphenols, hexylresorcinol, hexachlorophene, and phenol; quaternary ammonium compounds such as quaternary morpholinium alkyl sulfates, cetylpyridinium chloride, alkyldimethyl benzylammonium chloride, and alkyltrimethylammonium halides; and miscellaneous antibacterial components such as benzoic acid, formaldehyde, potassium chlorate, tyrothrycin, gramicidin, iodine and iodine liberating compounds, and oxygen-bearing compounds such as sodium perborate, and urea peroxide. These compounds, however, have either a disagreeable taste, or are significantly effective only at levels where they cannot be effectively masked by flavorants. Many have been removed from the market by FDA action. Some are incompatible with other mouthwash ingredients, while still others have high and undesirable toxicity or sensitization potential or are otherwise under suspicion of being unsafe for unsupervised human use.

Thus, presently available mouthwashes that are effective against bacterial suffer generally from the single major deficiency that they are at best physiologically unacceptable to many users and perhaps could present some potential hazard under certain conditions. At the very minimum a product must be acceptable to the user if it is to be used to full advantage.

It is therefore an object of the instant invention to provide for an antibacterial mouthwash that is physiologically acceptable to the user.

It is a further object of the invention to achieve physiological acceptance by not relying upon conventional germicide agents to provide antibacterial action.

These and other objects of the invention which will become readily apparent in the continuing discussion below are provided for in Applicants' present invention which in one of its broadest aspects provides for physiologically acceptable, germicide free, stable liquid mouthwash comprising (a) about 5 to 15 percent, by weight of said mouthwash, of ethanol;

(b) about 0.1 to about 2 percent, by weight of said mouthwash, of an essential oil flavor mixture selected from the group consisting of spearmint, peppermint and mixtures thereof;

(c) about 0.1 to about 0.6 percent, by weight of said mouthwash, of an alkyl sulfate anionic surfactant mixture wherein:

(i) said mixture consists essentially of dodecyl sulfate salt and a tetradecyl sulfate salt wherein the cationic moiety of said salts is selected from the group consisting of sodium, potassium, magnesium, ammonium, and substituted ammonium ions and mixtures thereof, and (ii) wherein said dodecyl sulfate is present in said mixture in a weight ratio to said tetradecyl sulfate of about 4:1 to about 1:1

(d) 0 to about 3 percent, by weight of said mouthwash, of a nonionic emulsifier;

(e) 0 to about 25 percent, by weight of said mouthwash, of a humectant;

(f) 0 to about 2 percent, by weight of said mouthwash, of an alkali metal halide;

(g) 0 to about 2 percent, by weight of said mouthwash, of a buffering salt pair, wherein said salt pair is capable of buffering said mouthwash to a pH of about 3 and about 8;

(h) 0 to about 2 percent, by weight of said mouthwash, of sodium saccharine, or an amount sufficient to provide a sweetening effect equivalent thereto of a sweetening agent; and (i) water.

The composition as set forth above provides for a highly acceptable pleasant tasting mouth rinse that at the same time affords a high degree of antibacterial action. Additionally, this unique and specific combination affords several unique benefits heretofore unexpected that will become apparent in the detailed description of the invention to follow.

STATE OF THE ART

It is known that the same surface active agents, in particular the quaternary ammonium compounds discussed above, are toxic to bacteria based upon their ability to disrupt the permeability properties of the bacteria's cellular interface. Also included besides the quaternaries are certain anionic detergent actives and certain other miscellaneous antibacterial compounds as set forth above.

While the theory is unconfirmed and while Applicants would not wish to be bound by the theory, it is believed that these agents probably disrupt permeability properties of the bacteria by combination with the phosphate groups in the phosolipids of the cytoplasmic membrane of susceptible bacteria. Among the anionic surface active agents that have been heretofore shown to demonstrate only a limited antibacterial activity is included sodium lauryl sulfate or more precisely sodium dodecyl sulfate. A complete discussion of these demonstrated activities is set forth in Lamanna et al.; *Basic Bacteriology;* 3rd. edition; the Williams and Welkins Company; 1965; Baltimore; pp 921–925, which is incorporated herein by reference.

Various alkyl sulfates and in particular sodium lauryl sulfate have received wide use in various oral hygiene products, however, these agents have been employed infrequently in mouthwashes per se. When employed in mouth rinses they always have been employed for their foaming properties and when so with noted difficulty.

Scanlen et al., U.S. Pat. No. 3,044,939; Menhart et al., U.S. Pat. No. 3,250,686; McCane et al., U.S. Pat. No. 3,488,419; Ergen, U.S. Pat. No. 3,497,590; Januszewski et al., U.S. Pat. No. 3,641,238; Prussin, U.S. Pat. No. 3,954,962; and Howell, U.S. Pat. No. 3,962,417 discuss various aspects of the employ of sodium lauryl sulfate in dentifrice formulations.

Davies et al., U.S. Pat. No. 3,087,857 disclosed a formulation containing 2 percent sodium lauryl sulfate to clean and remove odors from the mouths of dogs. The sodium lauryl sulfate is present to provide a cleansing effect as deodorancy and antibacterial action is provided by the inclusion of preservatives and bacteriocidal agents such as soluble penicillin and neomycin.

Moeller et al., U.S. Pat. No. 3,644,613 discloses mouthwashes containing 0.1 to 2 percent of a sudsing agent; however, it is apparent that the sole function of the sudsing agent is to supply foam and that the character of the sudsing agent is not critical.

Lavinsky et al., U.S. Pat. No. 3,462,525 discloses the use of olefin sulfonates as a replacement for sodium lauryl sulfates which are objectionable due to well noted "orange juice effects".

Thus while the art provides many varied mouthwash formulations none provide adequately for a stable liquid, physiologically acceptable, germicide free, antibacterial mouthwash.

DETAILED DESCRIPTION OF THE INVENTION

Applicants have now discovered that a stable liquid, physiologically acceptable, germicide free, antibacterial mouthwash can be achieved through a composition which in one of its broader aspects comprises:

(a) about 5 to about 15 percent by weight of said mouthwash, of ethanol;

(b) about 0.1 to about 2 percent, by weight of said mouthwash, of essential oil flavor mixture; selected from the group consisting of spearmint, peppermint and mixtures thereof;

(c) about 0.1 to about 0.6 percent, by weight of sad mouthwash, of an alkyl sulfate anionic surfactant mixture wherein:

(i) said mixture consists essentially of a dodecyl sulfate salt and a tetradecyl sulfate salt wherein the cationic moiety of said salt is selected from the group consisting of sodium, potassium, magnesium, ammonium, and substituted ammonium ions and mixtures thereof; and (ii) wherein said dodecyl sulfate is present in said mixture in a weight ratio to said tetradecyl sulfate of about 4:1 to about 1:1;

(d) 0 to about 3 percent, by weight of said mouthwash, of a nonionic emulsifier;

(e) 0 to about 25 percent, by weight of said mouthwash, of a humectant;

(f) 0 to about 2 percent, by weight of said mouthwash, of an alkali metal halide;

(g) 0 to about 2 percent, by weight of said mouthwash, of a buffering salt pair, wherein said salt pair is capable of buffering said mouthwash to a pH of between about 3 and about 8;

(h) 0 to about 2 percent, by weight of said mouthwash, of sodium saccharin, or an amount sufficient to provide a sweetening effect equivalent thereto of a sweetening agent; and (i) water.

As can be noted from the above, the most critical elements of the formulation of the invention are the alcohol, the flavor, the detergent mixture and of course the water base.

While the above formulation is open to the inclusion of various other ingredients that will not detract from its effectiveness, stability, germicidal activity or physiological acceptance the formulation in, of itself, represents a complete and viable composition and therefore in a narrower sense a stable liquid, physiologically acceptable, germicide free, antibacterial mouthwash can be achieved through a composition which consists essentially of:

(a) about 5 to about 15 percent, by weight of said mouthwash, of ethanol;

(b) about 0.1 to about 2 percent, by weight of said mouthwash, of an essential oil flavor mixture selected from the group consisting of spearmint, peppermint and mixtures thereof;

(c) about 0.1 to about 0.6 percent, by weight of said mouthwash, of an alkyl sulfate anionic surfactant mixture wherein:

(i) said mixture consists essentially of a dodecyl sulfate salt and a tetradecyl sulfate salt wherein the cationic moiety of said salt is selected from the group consisting of sodium, potassium, magnesium, ammonium, and substituted ammonium ions and mixtures thereof; and (ii) wherein said dodecyl sulfate is present in said mixture in a weight ratio to said tetradecyl sulfate of about 4:1 to about 1:1;

(d) 0 to about 3 percent, by weight of said mouthwash, of a nonionic emulsifier;

(e) 0 to about 25 percent, by weight of said mouthwash, of a humectant;

(f) 0 to about 2 percent, by weight of said mouthwash, of an alkali metal halide;

(g) 0 to about 2 percent, by weight of said mouthwash, of a buffering salt pair wherein said salt pair is capable of buffering said mouthwash to a pH of between about 3 to about 8;

(h) 0 to about 2 percent, by weight of said mouthwash, of sodium saccharin, or an amount sufficient to provide a sweetening effect equivalent thereto of a sweetening agent; and (i) water.

Again, while in this more narrow aspect of the invention, the formulation is still open to the inclusion of a more limited number of additional ingredients that will not materially change the attributes of the product, the formulation in of itself, with possibly the inclusion of colorants to provide an attractive appearance to the product, represents a complete and viable composition without the inclusion of any additional agents. Therefore in an even more narrow sense a stable liquid, physiologically acceptable, germicide free, antibacterial mouthwash can be achieved through a composition consisting of:

(a) about 5 to 15 percent by weight of said mouthwash, of ethanol;

(b) about 0.1 to about 2 percent, by weight of said mouthwash, of an essential oil flavor mixture selected from the group consisting of spearmint, peppermint and mixtures thereof;

(c) about 0.1 to about 0.6 percent, by weight of said mouthwash, of an alkyl sulfate anionic surfactant mixture wherein:

(i) said mixture consists essentially of a dodecyl sulfate salt and a tetradecyl sulfate salt wherein the cationic moiety of said salt is selected from the group consisting of sodium, potassium, magnesium, ammonium, and substituted ammonium ions and mixtures thereof; and (ii) wherein said dodecyl sulfate is present in said mixture in a weight ratio to said tetradecyl sulfate of about 4:1 to about 1:1;

(d) 0 to about 3 percent, by weight of said mouthwash, of a nonionic emulsifier;

(e) 0 to about 25 percent, by weight of said mouthwash, of a humectant;

(f) 0 to about 2 percent, by weight of said mouthwash, of an alkali metal halide;

(g) 0 to about 2 percent, by weight of said mouthwash, of a buffering salt pair wherein said salt pair is capable of buffering said mouthwash to a pH of between about 3 and 8;

(h) 0 to about 2 percent, by weight of said mouthwash, of sodium saccharin, or an amount sufficient to provide a sweetening effect equivalent thereto of a sweetening agent; and (i) water.

As noted above, Applicants' invention is a stable liquid, physiologically acceptable, germicide free, antibacterial mouthwash. These criteria are essential to the invention herein and the terminology is specific to the invention.

By the term "stable liquid" Applicants mean that the resulting product is a water clear liquid solution which is capable of undergoing prolonged storage under reduced temperature. While storage at elevated temperatures associated with shipment of the product, warehouse and commercial storage has not been found to produce any significant risk to the product stability, transportation, and storage of the product at reduced temperatures associated with specific seasonal climates in certain regions where the products of this type may be used has been shown to contribute to problems of stability. Specifically, extended storage at temperatures around 35° F. or less has an unstable product which is highly unattractive to the potential user, and importantly, a product whose lack of predictability reduces the manufacturer' confidence. Additionally, beyond physical appearance, clouding of the product can be associated with active materials coming out of solution and a product in this form can exhibit off flavor and can under adverse circumstances present a potential for tissue irritation as the result of tissue insult from contact with concentrated portions of otherwise diluted essential flavor oils. Accordingly, it is a minimum criterion that the stable mouthwashes of the instant invention be water clear and remain so under conditions of low temperature storage for extended periods of time. Specifically, for a mouthwash to meet the criterion of being a stable liquid, it must be water clear at the time of formulation and remain so after storage at 35° F. for a period of at least 7 days. Clarity is measured as the ability to resolve a grid of about 60 lines per inch by the naked eye when viewed through about 100 ml of the mouthwash contained in a 100 ml Nessler tube. In practice, an EXAX #45315 Nessler tube which is a glass cylinder closed at one end having a diameter of about 20 ml and an overall length of about 380 mm is filled with about 100 mls of the mouthwash to be tested (this will be a height of about 290 mm). The tube is then placed over a grid containing about 60 lines per inch with the closed end contacting the grid. The grid in the form of a photographic resolution chart contains about 60 black lines on a field of white so that the width of the black lines and white spaces between said lines is about the same. If the observer looking into the open end of the tube can then resolve the pattern of the grid, the product is adjudged to be water clear and hence stable. Conversely, inability to resolve the grid indicates that the mouthwash is not stable under the conditions tested.

By the term germicide free, Applicants mean that the mouthwash of the instant invention is free from the known and conventional germicides perviously associated with mouthwash.

As stated previously, mouthwashes having antibacterial activity generally contain chemical compounds known to be active against a wide spectrum of micro organisms. With the exception of those rinses which rely on certain flavor components such as oil of cinnamon, cassia, clove, eucalyptus, thyme, peppermint, anise, and wintergreen as well as the derivatives of these oils such as menthol, thymol, eucalyptol, anethole and methyl salicylate, to provide some minimal antibacterial effect, these rinses generally contain one or more compounds selected from categories of useful phenol compounds and quaternary ammonium compounds. The useful phenol compounds include (but are not limited to) for example beta naphthol, thymol, carvacrol, chlorothymol, amyl-, hexyl-, heptyl-, and octylphenols, hexylresorcinol, hexachlorphene and phenol itself. Examples of commercially important quaternary compounds incude cetylpyridinium chloride and alkyldimethylbenzylammonium chloride. Additional known antibacterial agents not under these general headings include for example benzoic acid, formaldehyde, potassium chloride, tyrothrycin, gramicidin, iodine and iodine liberating compounds, boric acid, chlorine liberating compounds, 8-hydroxyquinoline, nitrofurazine, organic mercury compounds, sodium perborate, urea peroxide and other oxygen liberating compounds. Thus, with the possible exception of a few flavor ingredients which will not be present at a level sufficient to contribute any significant antibacterial action, the mouthwash of the instant invention will be free of known antibacterial agents as exemplified above.

By the term antibacterial, Applicants mean that the mouthwash of the instant will have demonstrable effectiveness against reducing organisms associated with the oral cavity in use. Further the demonstrable effectiveness will have to be shown for contact times reasonably associated with the contact times one would expect for use with such a product. The ability to produce at least about a 99 percent kill of microbes associated with the oral cavity within a contact time of one minute, preferably less than about 30 seconds and most preferably within less than about 15 seconds.

The method employed to determine the satisfaction of this criteria is the Bactericidal Contact Time Test. This test which will be discussed in the Examples to follow is amply set forth in Curry; "Bactericidal Activity Laboratory Test"; *Soap and Chemical Specialties;* March 1968; pp 40, 42 and 150.

Finally, by the term physiologically acceptable, Applicants mean that the mouthwash under conditions of intended use is safe and organoleptically tolerable in the oral cavity, having no significant side effects either orally or systemically when used as directed.

Applicants have now found that antibacterial mouthwashes, free of essentially all bitter flavor and containing those essential flavor oils which are the most associated with freshness by the general public can be prepared by employing various lauryl sulfate salts selected from the group consisting of sodium-, potassium-, magnesium-, ammonium-, and substituted ammonium lauryl sulfate and mixtures thereof in place of the customarily employed germicides discussed above. Applicants have further found that in addition to producing an antibacterial mouthwash, the resulting product is physiologically acceptable and in fact is readily accepted by the user. Interestingly, however, Applicants have discovered that a stable product can only be achieved when said dodecyl sulfate is present in said mouthwash in a critical ratio with a tetradecyl dodecyl sulfate. Unless these two ingredients are present in the proportions and ratios as set forth below, the resulting mouthwash will not be stable and will be subject to clouding precipitation upon storage at or below 35° F. for extended periods of time.

The mouthwash of the instant invention comprises a mixture of specific levels of ethanol, an essential oil flavor, a lauryl sulfate and a tetradecyl sulfate in a water base.

The water of the mouthwash serves as a fluid base and functions as a flushing medium to wash away food particles cleansed from the mouth by the mouthwash. The level of water content of the rinse should be about 90 percent to about 45 percent by weight of the product.

Additionally, the mouthwash contains an essential oil flavor mixture. The flavor mixture is limited to those selected from the group consisting of spearmint, peppermint and mixtures thereof which means the flavor is characterized by the fact that the flavor mixture contains at least one essential oil selected from the group consisting of spearmint and peppermint essential flavor oils. It should be noted that the specific choice of this type of flavor and the limitation thereto is made on the basis that this class of flavor is a highly desirable flavor to the consuming public as representing and furnishing a fresh mouth feel and more importantly since this flavor group comprises essential oils namely spearmint and/or peppermint which provide excellent persistent flavor notes effective for residual odor masking. It is important to note that this type of flavor system has heretofore had only limited and generally unsuccessful use in antibacterial mouthwashes since such flavors were heretofore believed to be incompatible with known germicides and more importantly were believed to be extremely difficult to solubilize at least if essential oils were being employed. Additionally when solubilized, if at all, such solubilization was achieved by the use of high levels of nonionic emulsifier which provided no added efficient benefit to the product and in many instances contributed to off flavor.

This point itself is worthy of further amplification as the discovery of the ability to use such essential oil flavor mixtures in an aqueous base without the use of a nonionic emulsifier or nonionic surfactant to keep them in solution is quite contrary to general beliefs held within this art field. Even more significant is the fact that this solubility is achieved at relatively low levels of anionic surfactant.

Heretofore it was believed that flavor mixtures of this kind could only be held in solution by the use of exceedingly high levels of surfactants, levels of at least 2 percent, or more, which levels when employing the anionic surfactants and in particular alkyl sulfates were known to be potentially harmful in a product of this kind. While levels of sodium lauryl sulfate in this higher range have been employed in toothpaste products, use of such levels have been unacceptable in mouthwashes for safety reasons. Thus for all intended purposes the stabilization of essential mint oils in an aqueous base by using small amounts (i.e. about 0.1 to less than 1 percent) of a lauryl sulfate was heretofore believed impossible.

Applicants surprisingly have found that substantial amounts of such flavors, i.e. about 0.1 to about 2 percent, preferably about 0.1 to about 0.75 percent and most desirably about 0.2 to about 0.5 percent by weight of a substantially aqueous solution can be solubilized by the inclusion in said solution of about 0.1 to about 0.6 percent, by weight of said mouthwash, of an alkyl sulfate anionic surfactant mixture wherein said mixture consists essentially of a dodecyl sulfate salt and a tetradecyl sulfate salt wherein the cationic moiety of said salts is selected from the group consisting of sodium, potassium, magnesium, ammonium, and substituted ammonium ions and mixtures thereof, and wherein said dodecyl sulfate is present in said mixture in a weight ratio to said tetradecyl sulfate of about 75:1 to about 1:1. By substantial aqueous solution, Applicants mean that the solution contains about 45 to about 90 percent water and contains no more than about 15 percent ethanol or other alcohol. Thus, Applicants suprisingly have found that with their system of using a dodecyl sulfate in conjunction with a tetradecyl sulfate as a replacement for known germicides, they are now able to solubilize this flavor group as well as provide antibacterial activity. Additionally, and more suprisingly, this end has been achieved with remarkably low levels of these sulfates and without the need for additional nonionic emulsifiers.

It has been found that the flavor mixture may be present in an amount of about 0.1 to about 2 percent by weight of said mouthwash. Preferably, the level of the flavor should be about 0.1 to about 0.75 percent. More desirably, the flavor should be present at a level of about 0.2 to about 0.5 percent with the most desirable level being about ¼ of one percent.

The flavorant is characterized by containing major portions of menthol, methyl salicylate, oil of peppermint, and spearmint oil both natural and synthetic along with various flavor modifiers which the maker may wish to employ to give his product a distinctive note.

By a major portion is meant at least about 50 percent of the flavor mixture should be made up by at least one or a mixture of these ingredients.

Accordingly, another aspect of Applicants' discovery can be interpreted as an antibacterial, germicide free, physiologically acceptable essential oil flavored mouthwash comprising:

(a) 45 to about 85 percent by weight of said mouthwash of water;

(b) less than about 20 percent by weight of said mouthwash of ethanol;

(c) about 0.1 to about 2 percent by weight of an essential oil flavor said flavor comprising at least 50 percent by weight of its composition of at least one essential oil selected from the group consisting of spearmint and peppermint oil;

(d) about 0.1 to about 0.6 percent, by weight of said mouthwash, of an alkyl sulfate anionic surfactant mixture wherein:

(i) said mixture cnsists essentially of a dodecyl sulfate salt and a tetradecyl sulfate salt wherein the cationic moiety of said salts is selected from the group consisting of sodium, potassium, magnesium, ammonium, substituted ammonium and morpholenium ions and mixtures thereof, and (ii) wherein said dodecyl sulfate is present in said mixture in a weight rato to said tetradecyl sulfate of about 75:1 to about 1:1;

(e) 0 to about 3 percent, by weight of said mouthwash, of a nonionic emulsifier;

(f) 0 to about 25 percent, by weight of said mouthwash, of a humectant;

(g) 0 to about 2 percent, by weight of said mouthwash, of an alkali metal halide;

(h) 0 to about 2 percent, by weight of said mouthwash, of a buffering salt pair, wherein said salt pair is capable of buffering said mouthwash to a pH of between about 3 and 8; and (i) 0 to about 2 percent, by weight of said mouthwash, of sodium saccharin, or an amount sufficient to provide a sweetening effect equivalent thereto of a sweetening agent. This interpretation is subject to the same limitations with respect to limitations on preferred ranges on optional ingredients, i.e. ingredients which may be included at a 0 percent level as set forth previously and to be discussed in the remainder of the disclosure to follow.

As will be noted the critical ratio of dodecyl to tetradecyl sulfate of this aspect of the invention is somewhat broader than that disclosed for the stable aspect of the solution and it should be expected that in ratios substantially greater than about 4:1 that some difficulty can be expected with respect to low temperature storage. However, if such low temperature storage can be avoided the resulting product should remain water clear. Thus should low temperature storage not be a criticality, the above disclosed aspect of the invention should provide a pleasant tasting, essential oil flavored mouthwash which is antibacterial yet germicide free.

The function of the ethanol is to add bite and refreshment to the mouthwash and may in some instances, in a limited way, act to enhance the solubilization of certain flavor oils. Secondly, the alcohol enhances the cleansing efficacy. Generally, the mouthwash should contain about 5 to about 20 percent by weight of ethanol. Preferably, however, the rinse should contain about 10 to about 15 percent. More desirably, the rinse should contain about 12 to about 13 percent of the alcohol with about 12 and ½ percent being the most desirable level of incorporation. All levels of alcohol are expressed as percent 190 proof alcohol contained in the mixture.

While it has been known that sodium dodecyl sulfate will exhibit some antibacterial activity, use of such an active for the replacement of high active germicides in a mouthwash was heretofore uncontemplated in the art. Generally, it was believed that levels associated with efficient killing action would be intolerable to the user, i.e. levels of more than one percent. Applicants have found that levels of lauryl sulfates approaching one percent are indeed too high to be tolerable in a mouthwash product. Applicants, however, have discovered that more than adequate antibacterial action can be achieved at levels much lower than heretofore believed as measured against the aforestated criteria. These ranges will be set forth below.

Interestingly, Applicants have discovered that mouthwashes formulated with these key ingredients are unstable under conditions of low temperature storage. Specifically, mouthwashes comprising water, about 5 to about 15 percent ethanol, about 0.1 to about 2 percent of a essential mint oil flavor mixture and a low level, i.e. about 0.1 to about 0.6 percent, of dodecyl sulfate are not stable after storage at 35° F. for one week. Applicants have discovered, however, that by incorporating a critical amount of tetradecyl sulfate with the dodecyl sulfate a stable formulation can be achieved. Thus in its broadest application, the stable mouthwash should contain about 0.1 to about 0.6 percent by weight of a mixture of a dodecyl sulfate and a tetradecyl sulfate wherein the dodecyl sulfate is present in a ratio to the tetradecyl sulfate of about 4:1 to about 1:1. Outside these limitations, less than satisfactory stability is obtained although as mentioned above, if cold temperature storage is not a potential problem, ranges of about 75:1 to about 1:1 can be employed. Levels of alkyl sulfate less than the level of about 0.1 percent do not demonstrate adequate antibacterial activity or solubilizing effect of the flavoring oils, and levels much higher than about 0.6 percent present the potential for lack of physiological acceptability.

While sodium dodecyl sulfate and sodium tetradecyl sulfate are the preferred salt forms the cationic moiety of the respective salts may be selected from the groups consisting of sodium potassium, magnesium, ammonium, and substituted ammonium ions and mixtures thereof.

While a level of the alkyl sulfate mixture of between about 0.1 to about 0.6 is adequate, it is preferred to have the sulfate mixture present at a level of about 0.2 to about 0.4 percent with the most desirable level being about 3/10 of one percent.

Nonionic emulsifiers may be included to modify flavor effect and initial taste. These ingredients are customarily added to conventional mouthwashes to solubilize flavor. Due to the nature of the instant invention, they are not required for this purpose, however, they have been found in the present invention to provide some degree of flavor modification effect. Generally, these emulsifiers may be employed at a level of from 0 to about 3 percent by weight of said mouthwash; however, it is preferable to employ at least about 0.1 percent. More desirable, it has been found to employ about 0.1 to about 0.5 percent of these agents. More preferably, about 0.2 to about 0.4 percent can be employed with the most desirable level being about ¼ of one percent. While the exact emulsifier is not critical, one should be cautioned that not all nonionic emulsifiers will work, and in fact some will seriously detract from stability. Known to provide adequate results are such nonionic emulsifiers such as polyoxyethylene 20 sorbitan monolaurate, polyoxyethylene 20 stearyl ether, polyoxyethylene 20 isohexadecyl ether, polyoxyethylene 100 stearate, polyoxyethylene 10 stearyl ether and mixtures thereof. Polyoxyethylene 20 sorbitan monolaurate is the preferred nonionic emulsifier. While not all of the commercially available emulsifiers will work, these compounds are very familiar to one skilled in the art and it is a simple task for one skilled in the art to determine those which will be compatible. While the aforementioned disclosure of various emulsifiers will work, Applicants in no way wish to suggest that their invention is limited to just these emulsifiers as any nonionic emulsifier that will provide a benefit and that is compatible to the whole formulation is within the scope of the invention.

Humectants may be incorporated at levels of from 0 to about 25 percent by weight of said mouthwash. The function of the humectant is primarily to add "body" or mouthfeel to the mouthwash thereby making it more pleasant to use. As with the nonionic emulsifiers these compounds are readily familiar to those skilled in the art and many variations of these ingredients can successfully be employed by one skilled in the art with simple experimentation.

Preferably, the humectant should be present at a level of at least about 5 percent. Preferably, the humectant should be present at a level of about 5 to about 20 percent. Desirably, the humectant should be present at a level of about 10 to about 15 percent with the most desirable level being about 12 percent with the most preferred humectant being sorbitol. Additional humectants that are subject to the instant invention include but are not limited to glycerol, propylene glycol and corn syrup.

An alkali metal halide, preferably sodium chloride may be present from 0 to about 2 percent by weight of the mouthwash. The halide salt serves as an electrolyte and contributes to the overall flavor. Preferably, this salt should be present at a level of about 0.01 to about 0.1 percent with the most desirable level being about 5/100 of one percent.

Additionally, the mouthwash may contain a buffering salt pair to control the pH of the final product. The composition of the salt pair is highly variable and one skilled in the art can with simple experimentation arrive at various salt pairs that will be functional and that will not detract from the overall compositions. Generally, the salt pair should be capable of buffering the mouthwash to a pH of between about 3 and about 8 and should be present in said mouthwash at a level of 0 to about 2 percent. Preferably, the buffering salt pair should be present at a level of about 0.01 to about 0.1 percent with the most desirable level being about 5/100 of one percent. The preferred salt pair is a mixture of sodium acetate and acetic acid. When employing this mixture, the ratio of the sodium acetate to the acetic acid can vary widely so long as the resultant ratio is capable of producing a pH within the desired range. Preferably, however, the ratio of sodium acetate to acetic acid is about 3:2.

Artificial sweeteners, as well as natural sweeteners, may be employed to round out the resulting product as many users prefer a sweeter product than one containing just essential oil flavors. While sodium saccharin is the preferred sweetening agent, any compatible sweetening agent is contemplated within the scope of the invention. When employing sodium saccharin 0 to 2 percent by weight of said mouthwash may be employed. In employing any other compatible sweetening agent, any amount equivalent to producing an equivalent level of sweetening to the 0 to about 2 percent sodium saccharin will suffice. Preferably, the mouthwash will contain about 0.01 to about 0.5 percent sodium saccharin or an amount sufficient to provide a sweetening effect equivalent thereto of another sweetening agent. More desirably, the mouthwash should contain about 0.05 to about 0.075 percent of sodium saccharin or an amount sufficient to provide a sweetening effect equivalent thereto of another sweetening agent with the most desirable level being about 5/100 of a percent. Additionally, any mixture of sweetening agents having an equivalent sweetening effect and compatible to the whole formulation is contemplated within the term sweetening agent.

While the manner of mixing the ingredients of mouthwash is not critical, it is preferred to prepare alcohol and water phase premixes and to then mix these phases. More preferably, the alcohol premix should contain only a portion of the alcohol of the product with the remaining alcohol of the product being added subsequent to the comixing of the two premixes. Filtration may be employed at this point to enhance the clarity of the resulting product. Generally, the alcohol phase should comprise at least a portion of the alcohol of the final product, the flavor mixture and the nonionic emulsifier if an emulsifier is going to be employed. The water phase should contain the water and the alkyl sulfate mixture and if employed the sweetening agent, the alkali metal halide salt, the buffering salt pair, the humectant and colorant if desired. The actual mixing techniques are highly variable and can readily be determined by one skilled in the art of compounding such formulations with simple expermentation in light of the equipment available to him.

The resulting product will be a clear stable, physiologically acceptable, germicide free mouthwash having antibacterial action. Applicants have found that the mouthwash will produce bacteria reduction in the mouth at least equivalent to the degree of reduction brought about by commercially available mouthwashes containing quaternary germicides. Additionally, Applicants have suprisingly discoverd that the resulting mouthwash is especially effective at reducing mal odor in the mouth associated with the ingestion of foods containing onion and garlic, an effect obtained with a relatively low level of alcohol and without bitter or astringent substances and an effect heretofore not demonstrated by conventional mouthwashes.

Accordingly, the mouthwash of the instant invention provides a physiologically acceptable method of reducing bacteria and/or the mal odor in the mouth associated with the ingestion of foods containing either onion or garlic or a combination thereof said method comprising contacting the tissue of the oral cavity, for a time sufficient to reduce said mal odor and/or said bacteria, with the mouthwash of the invention. Generally, it has been found that a contact time of less than about 15 seconds is sufficient, however, it is preferred that the contact time be about 30 seconds. Additional contact time will increase the effect, however, contact times longer than one minute will not be practical to the user and the rinse has accordingly been designed to produce the desired effect in 30 seconds or less, preferably about 15 seconds.

Various examples illustrative of the invention are presented as follows and are no way to be considered as limiting the scope of the invention which is capable of countless variations.

All parts given are by weight unless specified otherwise.

EXAMPLE 1

A mouthwash comprising a water base containing 12.5 percent ethanol, 0.25 percent of an essential oil flavor mixture comprising a mixture of predominently spearmint and peppermint essential oils and 0.3 percent of sodium dodecyl sulfate was prepared by first dissolving the flavor oils in the alcohol and second dissolving the sodium lauryl sulfate and thirdly comixing the alcohol and water premixes. The result was a turbid suspension at room temperature that would not clear. A GLC analysis of this sodium dodecyl sulfate indicated the following composition of alkyl sulfate homologs:

Sodium dodecyl sulfate; 99.7 percent
Sodium tetradecy sulfate; 0 percent
Miscellaneous impurities; 0.3 percent As can be seen, a pure sodium dodecyl sulfate will not solubilize an essential oil flavor mixture.

EXAMPLE 2

A mixture according to Example 1 was compounded as per Example 1 this time substituting a sodium dodecyl sulfate-sodium tetradecyl sulfate composition as follows:

Sodium dodecyl sulfate; 97.5 percent
Sodium tetradecyl sulfate; 1.3 percent
Miscellaneous $C_{10}C_{16}$ and $C_{18}$ sulfates; 1.2 percent total The resultant mixture produced a stable water clear solution. 100 cc of the solution was transferred to a EXAX # 45315 Nessler tube having an end diameter of about 20 mm. The closed end of the tube was placed upon a 60 line per inch grid. The 60 line grid could readily be observed through the tube.

The solution was cooled to 35° F. whereupon the above procedure was repeated. At this point difficulty was encountered in observing the grid.

From the above it is clear that a mixture of docecyl sulfate and tetradecyl sulfate in a ratio of about 75:1 will produce a clear mouthwash at room temperature, however, fails to produce a stable mouthwash under conditions of reduced temperature and extended storage.

EXAMPLE 3

The mixture of Example 1 was repeated and the test evaluation of Example 2 was repeated upon the resulting mouthwash was repeated for alkyl sulfate mixtures 3A, 3B and 3C. The homolog distribution of the alkyl sulfates were as follows:

|  | 3A | 3B | 3C |
|---|---|---|---|
| Sodium decyl sulfate | Trace | Trace | Trace |
| Sodium dodecyl sulfate | 65.5% | 71.5% | 66.9% |
| Sodium tetradecyl sulfate | 27.1% | 28.2% | 32.9% |
| Sodium hexadecyl sulfate | 7.3% | Trace | Trace |

The resulting mouthwashes were water clear and stable at room temperature and remained so after 7 days at 35° F.

EXAMPLE 4

Fourteen solutions coeded 4A to 4N were made up as follows:

| Code | Percent dodecyl sulfate tetradecyl sulfate mixture having a $C_{12}/C_N$ ratio between about 4:1 to 1:1 | Percent doublemint essential oil flavor mixture* | Ethanol |
|---|---|---|---|
| 4A | 0 | 0 | 12.5 |
| 4B | 0 | 0.25 | 12.5 |
| 4C | 0.08 | 0 | 0 |
| 4D | 0.08 | 0 | 12.5 |
| 4E | 0.08 | 0.25 | 0 |
| 4F | 0.08 | 0.25 | 12.5 |
| 4G | 0.3 | 0 | 0 |
| 4H | 0.3 | 0 | 12.5 |
| 4I | 0.3 | 0.25 | 0 |
| 4J | 0.3 | 0.25 | 12.5 |
| 4K | 0.6 | 0 | 0 |
| 4L | 0.6 | 0 | 12.5 |
| 4M | 0.6 | 0.25 | 0 |
| 4N | 0.6 | 0.25 | 12.5 |

*a mixture containing a mixture of spearmint and peppermint essential oils.

The resulting solutions were evaluated for stability according to the procedure set forth in Example 2 both at initial room temperature and after 7 days at 35° F.

The resulting solutions were then evaluated for bacterial activity under the Bactericidal Contact Time (BCT) test method as follows:

1. 1 ml of stock (A) is placed in a medication tube (25×100 mm) in a rack held at the desired temperature.

2. 1 ml of culture preparation (B) is added and timing started using a stop watch. For multiple testing, mixtures can be inoculated at 15-second intervals and sampled accordingly.

3. Breed calibrated loops (Will Corp.) are used for withdrawing samples at predetermined intervals. If, by design, the initial count is $10^7$/ml, a 0.001 ml loop is used; if $10^6$/ml, a 0.01 ml loop is used. Several loops should be used in rotation to allow time to cool after flaming.

4. Each loop sample is immediately placed into 5 ml molten agar in oval tubes (special order, Bellco Glass, Inc.), held at ca. 48° C. in a water bath. The use of Morton closures allows for ease in manipulation of tubes during performance of the test. Racks are obtainable from George H. Wahmann Mfg. Co., Baltimore.

5. Although any rich medium serves the purpose, we favor Microinoculum Broth + 1.5% agar. The clarity of the medium is exceptional, its richness fosters the development of large discrete colonies, and no additional neutralizers are apparently necessary. If desired, Letheen Agar can be used. In our experience, however, we have not found a need for it, since no carry-over effects have occurred in practice. Also, the clarity of Letheen Agar is poor, and colonies which develop on it are much smaller and therefore more difficult to count.

6. The agar containing the sample is gently mixed and the tube slanted in a rack to allow hardening. The rack of tubes is then inverted and incubated at 37° C. for colony development. Counts are made in the same manner as standard plate counts, employing an oval tube adapter (1957) for the Quebec Colony Counter for ease in counting.

7. Initial density of organisms is determined by diluting culture preparations (B) $10^3$. On ml of this dilution is added to 1 ml of sterile 0.1% peptone water (instead of test solution) in a control medication tube and sampled in replicates (at least 3) by appropriate loop. The average colony count obtained represents the 99.9% endpoint in any of the test mixtures. Table 1 illustrates the mathematics involved to arrive at this endpoint. If of interest, a count of onetenth tht in the control would be the 99.99% endpoint.

8. Carry-over effect can be determined by transferring a loop of uninoculated test mixture, and a loop of the $10^{-3}$ control culture dilution, to replicate oval tubes. If bacteriostasis is evident, a more efficient neutralizing medium should be used in subsequent runs. Since we have never found this to be necessary, we no longer include this control unless confronted with new systems of unknown inactivation potential.

9. To equate the BCT test with the Chambers Test (1956, 1965), the initial count should be $10^8$/ml and a 0.01 ml loop would be employed to an endpoint of 99.99% kill.

10. Results are recorded as a function of time to effect a certain degree of kill, rather than as percent reduction values after a set time interval.

TABLE I

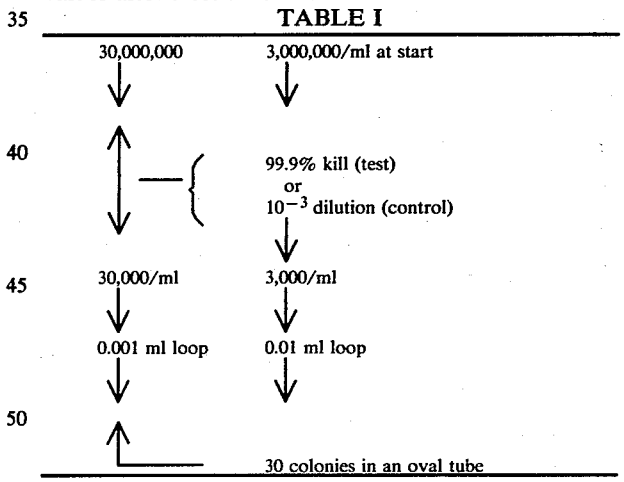

Additionally, all were evaluated for physiological acceptability.

Results of these evaluations are shown in Table 2.

TABLE 2

| | Comparison of Levels of Alkyl sulfate Mixtures | | | | | | |
|---|---|---|---|---|---|---|---|
| CODE | Percent Alkyl sulfate mixture having a $C_{12}/C_{14}$ between 4:1 to 1:1 | Percent Double-mint Flavor | Percent Ethanol | Stability Initial | Stability 35° F./7 days | BCT Time to 99.9% kill | Physiological Acceptability |
| 4A | —0— | —0— | 12.5 | >60 | >60 | >5 min. | A |
| 4B | —0— | 0.25 | 12.5 | <5 | <5 | >5 min. | UA |
| 4C | 0.08 | —0— | —0— | >60 | >60 | >5 min. | UA |
| 4D | 0.08 | —0— | 12.5 | >60 | >60 | >5 min. | UA |

TABLE 2-continued
Comparison of Levels of Alkyl sulfate Mixtures

| CODE | Percent Alkyl sulfate mixture having a $C_{12}/C_{14}$ between 4:1 to 1:1 | Percent Double-mint Flavor | Percent Ethanol | Stability Initial | Stability 35° F./7 days | BCT Time to 99.9% kill | Physiological Acceptability |
|---|---|---|---|---|---|---|---|
| 4E | 0.08 | 0.25 | —0— | >60 | >60 | >5 min. | UA |
| 4F | 0.08 | 0.25 | 12.5 | <5 | <5 | >5 min. | UA |
| 4G | 0.3 | —0— | —0— | >60 | >60 | 15 sec. | UA |
| 4H | 0.3 | —0— | 12.5 | >60 | >60 | 15 sec. | UA |
| 4I | 0.3 | 0.25 | 13 0— | >60 | >60 | 15 sec. | UA |
| 4J | 0.3 | 0.25 | 12.5 | >60 | >60 | 15 sec. | A |
| 4K | 0.6 | —0— | —0— | >60 | >60 | 15 sec. | UA |
| 4L | 0.6 | —0— | 12.5 | >60 | >60 | 15 sec. | UA |
| 4M | 0.6 | 0.25 | —0— | >60 | >60 | 15 sec. | UA |
| 4N | 0.6 | 0.25 | 12.5 | >60 | >60 | 15 sec. | A |

*A = acceptable
UA = unacceptable

As can be seen form Table 2, less than 0.1 percent of the alkyl sulfate mixture could not stabilize the three-component mixture (4F) and none of the solutions showed an adequate kill time under the BCT test.

At the 0.3 percent level of alkyl sulfate mixture, all solutions were stable and produced excellent kill times under the BCT test. 4G was unacceptable as it was an unflavored detergent solution as was 4H. 4I was unacceptable as it lacked alcohol to provide bite.

At the 0.6 percent level of alkyl sulfate mixtures, all solutions were stable and produced excellent kill times under the BCT test. Solutions 4K, 4L and 4M were unacceptable for reasons similar to the corresponding 4G, 4H and 4J.

EXAMPLE 5

Male and female laboratory rats were treated four times daily for a period of four days with solutions having concentrations of commercial grade sodium lauryl sulfate of 0.1, 0.3 or 1.0 percent. The vehicle for these concentrations, 12 percent ethanol in water, was employed as a control. Treatment consisted of gently swabbing the interior of the mouth with 0.25 cc of the particular test solution for 30 seconds using an artists brush. The results of the test are shown in Table A.

TABLE 3
RESULTS OF RAT ORAL BRUSHING TEST

| Group | Rinse | Cumulative Average Irritancy Response Sloughing | Chelitis | Total |
|---|---|---|---|---|
| 1 | 12% ethanol in water | 0 | 0 | 0 |
| 2 | 0.1% sodium lauryl sulfate in 12% ethanol/water | 0.1 | 0.1 | 0.2 |
| 3 | 0.3% sodium lauryl sulfate in 12% ethanol/water | 0.3 | 0.4 | 0.7 |
| 4 | 1.0% sodium lauryl sulfate in 12% ethanol/water | 0.6 | 0.8 | 1.4 |

As can be seen, a significant relationship is observed between the dose administered and the effect produced. The 1.0 percent dose is considerably more irritating than the other doses administered.

EXAMPLE 6

Two mouthwash compositions, 6A and 6B were made up as follows:

| Ingredient | 6A % | 6B % |
|---|---|---|
| Ethanol, 190 proof | 12.5000 | 12.5000 |
| Doublemint essential oil flavor mixture | 0.2500 | 0.2500 |
| Polyoxyethylene 20 sorbitan monolaurate | 0.2500 | — |
| Sodium alkyl sulfate mixture ($C_{12}/C_{14}$ ratio about 2.5/1) | 0.3000 | 0.3000 |
| Sorbitol | 12.0000 | 12.0000 |
| Sodium saccharin | 0.0650 | 0.0650 |
| Sodium chloride | 0.0500 | 0.0500 |
| Sodium acetate | 0.0300 | 0.0300 |
| Acetic acid | 0.0200 | 0.0200 |
| Colorant | 0.00085 | 0.00085 |
| Water | To 100% | To 100% |

As can be seen, the formulations are identical with the exception that formula 6B does not contain a nonionic emulsifier.

Thirty panelists were divided randomly into two groups of fifteen. Each group rinsed with one ounce of one of the test mouthwashes for 30 seconds. Panelists were given a set of descriptors as follows below:

| | Very True | Mostly True | Slightly True | Not True |
|---|---|---|---|---|
| 1. Has a good refreshing feel | ( ) | ( ) | ( ) | ( ) |
| 2. Flavor comes on quickly | ( ) | ( ) | ( ) | ( ) |
| 3. Has the right amount of foam | ( ) | ( ) | ( ) | ( ) |
| 4. Leaves a pleaseant after taste | ( ) | ( ) | ( ) | ( ) |
| 5. Flav or was too harsh | ( ) | ( ) | ( ) | ( ) |
| 6. Made my mouth burn | ( ) | ( ) | ( ) | ( ) |
| 7. Caused too much foaming | ( ) | ( ) | ( ) | ( ) | and were asked to rate the attributes given on the basis of the four point scale.

About 45 minutes later the panelists repeated the test with the remaining rinse. Results were tabulated and statistically treated as shown in Table 4.

Table 4

| Descriptor | Descriptor Mean Scores 6A | 6B | Sig* |
|---|---|---|---|
| 1. Has a good refreshing feel | 3.4 | 3.3 | NS |
| 2. Flavor comes on quickly | 3.1 | 3.6 | 99% |
| 3. Has the right amount of foam | 3.1 | 3.1 | NS |
| 4. Leaves a pleasant aftertaste | 3.0 | 2.8 | NS |
| 5. Flavor was too harsh | 1.9 | 2.2 | NS |
| 6. Made my mouth burn | 2.2 | 2.8 | 97.5% |
| 7. Caused too much foaming | 1.2 | 1.4 | NS |

As can be seen from Table 4, there was a statistically significant difference between the products with respect to flavor attribute descriptors 2 and 6. It is readily apparent that the mouthwash variant without the nonionic emulsifier was perceived as being significantly more burning to the mouth.

Additionally, the panelists were asked to rank the mouthwashes on a thermometer scale of 10 to 100 with respect to overall acceptability. Mouthwash 6A received an average thermometer ranking of 67.8 (standard deviation 14.2) and mouthwash 6B received an average thermometer ranking of 67.5 (standard deviation 16.2). A score of 60 to 70 indicates a level of acceptance of "good" to "very good". No statistical differences existed between the two scores. Accordingly, the overall interpretation of the results was that while both mouthwashes were equally and generally well received, inclusion of a nonionic emulsifier in the product may be contemplated to help round out the overall flavor perception.

EXAMPLE 7

Mouthwash of the instant invention, and in particular, the formula given as 6A in Example 6 was compared to commercially available mouthwashes containing various known germicides under the following procedure:

Buccal Tissue Count Method

Approximately 12 subjects per product (13 were used on a control which was the mouthwash of the instant invention without alkyl sulfate) are recruited and instructed not to brush their teeth on the morning of the test, and to report to the test area as soon as they arrive on that morning. The test is then conducted as follows:

General Procedure

1. A curette sample of buccal tissue is first taken from each panelist, and transferred to 10 ml sterile 0.1% peptone water ($10^{-1}$ dilution of the sample) solution.

2. The subject then rinses with 15 ml of the mouthwash for 30 sec., followed by two brief water rinses, and a second sample of buccal tissue is taken immediately thereafter. The time of day is recorded on a card and a schedule prepared for return visits for each subject. This completes the product usage part of the test, and the panelists return according to interval-sampling schedules that they are given. At the times designated, they return to the test area for additional tissue sampling. All sample tubes are refrigerated between intervals.

3. Since bacterial counts return to baseline within 2 hrs., unless the product used contains an antibacterial agent, the schedule of interval-sampling is normally 2, 3 and 4 hrs. beyond zero-time for differentiation of test products. When testing non-antibacterial products, however, sampling intervals are narrowed to include a 1-hr., or even a ½ hr. post-usage sample.

4. The accumulated samples are then plated in Brian Heart Infusion Agar (or any other rich medium of choice) at dilutions appropriate to the product and interval represented. For antibacterial products, countable plates are normally obtained by the following dilution scheme:

| | | |
|---|---|---|
| Before | $10^{-3}$ and $10^{-4}$ | 0.1 ml (of $10^{-1}$ sample dilution) in 10 ml = $10^{-3}$; 1 and 0.1 ml plated. |
| After | $10^{-1}$ and $10^{-2}$ | 1 and 0.1 ml plated directly |
| 2 hrs. | $10^{-2}$ and $10^{-3}$ | 1 ml in 10 ml = $10^{-2}$; 1 and 0.1 ml plated |
| 3 hrs. | $10^{-3}$ and $10^{-4}$ | as the "before" sample |
| 4 hrs. | $10^{-3}$ and $10^{-4}$ | |

For non-antibacterial products, an appropriate dilution scheme is:

| | |
|---|---|
| Before $10^{-3}$ and $10^{-4}$ | |
| After $10^{-1}$ and $10^{-2}$ | |
| ½ hr. $10^{-2}$ and $10^{-3}$ | obtained in same manner as above |
| 1 hr. $10^{-2}$ and $10^{-3}$ | |
| 2 hrs. $10^{-3}$ and $10^{-4}$ | |
| 3 hrs. $10^{-3}$ and $10^{-4}$ | |

5. The finished plates are allowed to harden, inverted, and incubated (at 32° C.) for 7 days. Colonies are counted, converted to count $X10^3$/BT sample/subject, with the data computer. The analyses include group geometric means, % change from baseline per interval, P value and 95% confidence limits.

6. As a general rule, antibacterial products maintain a reduced count ($P \geq 0.95$) for at least 2 hrs. and are differentiated on the basis of how long the effect lasts. The effect of non-antibacterial products is normally lost within 2 hrs. The results of the test are shown in table 5.

TABLE 5

Comparison of Buccal Time Count Results

| | | | HOURS AFTER SINGLE USE | | | | |
|---|---|---|---|---|---|---|---|
| Product | Active | Criteria | 0 | ½ | 1 | 2 | 3 |
| Water | None | % reduction | 37.7 | | | | |
| | | P value | 0.98 | | | | |
| Control | None | % reduction | | 67.3 | 43.8 | −41.6 | −63.9 |
| | | P value | | 0.99 | 0.80 | 0.80 | 0.99 |
| 6A | 0.3% alkyl sulfate mixture | % reduction | 97.1 | 95.3 | 90.9 | 68.4 | 44.8 |
| | | P value | 0.99 | 0.99 | 0.99 | 0.99 | 0.99 |
| L₁* | zinc chloride | % reduction | 79.3 | 74.6 | 67.9 | −8.5 | −52.6 |
| | | P value | 0.99 | 0.99 | 0.99 | <0.75 | 0.95 |
| M* | Cetyl pyridinium chloride | % reduction | 99.9 | | | 86.9 | 57.4 |
| | | P value | 0.99 | | | 0.99 | 0.99 |
| S* | Cetyl pyrridinium chloride and Domiphene | % reduction | 99.9 | | 97.3 | 95.3 | 82.6 |
| | | P value | 0.99 | | 0.99 | 0.99 | 0.99 |

TABLE 5-continued

| | Comparison of Buccal Time Count Results | | | | | | |
|---|---|---|---|---|---|---|---|
| | | | HOURS AFTER SINGLE USE | | | | |
| Product | Active | Criteria | 0 | ½ | 1 | 2 | 3 |
| | bromide | | | | | | |

*$L_1$, M and S are commercially available mouthwashes.

As can be seen, the mouthwash of the instant invention (Code 6A) provides equivalent antibacterial activity to commercial products containing various known actives including cetylpyridinium chloride and domiphene bromide.

EXAMPLE 8

Gradient Plate (GP) tests were conducted to determine the antibacterial activity of fourteen anionic surfactants. The GP test employs a square phage-type petri dish which is placed on an inclined platform so that a base layer of agar can harden in the form of a wedge. A second layer of active contains the active in known dilution and is hardened with the plate in a level position. Dilution of the base layer due to diffusion from the second layer results in a concentration gradient onto which several organisms are streaked. The organisms tested include Richbergs Oral Staph*, Candida Albecans, *Streptococcus salivaricus,* antibiotic resistant Strep. and Leptotrichin which are all isolates associated with the oral cavity. After incubation growth fronts are measured and minimum inhibitory concentration values are calculated in terms of PPM active required to inhibit growth.

*These isolates were isolated from individuals employed at Lever Brothers Company, 45 River Road, Edgewater, New Jersey. These isolates were employed to demonstrate that the products tested demonstrated equivalent efficacy towards isolates obtained from individuals as those grown and supplied by commercial lab supply houses.

Results are shown in Table 5. As can be seen, the dodecyl sulfate provides the best average broad based inhibitory effect of the closely related homologs indicating a superiority of this particular chain length over the related homologs.

TABLE 5

| | Gradient Plate Evaluation | | | | | |
|---|---|---|---|---|---|---|
| | | PPM required to inhibit* | | | | |
| Ingredient | Activity | Rich. | Ca: | S. sal. | Anti. | Lepto. |
| sodium decyl sulfate | 100% | 1,800 | 2,000 | 1,900 | 2,100 | 1,800 |
| sodium dodecyl sulfate | 100% | 190 | 250 | 250 | 470 | 2,500 |
| sodium tetradecyl sulfate | 100% | 140 | 130 | 150 | 180 | 710,000 |
| sodium hexadecyl sulfate | 100% | 10,000 | 170 | 190 | 240 | 2,900 |

*Rich. = Richbergs Oral Staph - a mouth isolate
Ca. = *Candida albecans* - a yeast registered with ATCC No. 10231
S.sal. = *Strep. salavarious* - a mouth isolate registered with ATCC No. 9756
*Anti = Antibiotic resistant Strep. - a mouth isolate
*Lepto. = Leptotrichia - an antibiotic resistant mouth isolate
*These isolates were isolated from individuals employed at Lever Brother Company, 45 River Road, Edgewater, New Jersey. These isolates were employed to demonstrate that the products tested demonstrated equivalent efficacy towards isolates obtained from individuals as with commercial isolates.

EXAMPLE 9

A mouthwash according to the instant invention and more precisely a mouthwash according to formula Example 6 was evaluated against a commercial mouthwash of longstanding reputation as an effective mouthwash against oral mouth odor. This commercially available mouthwash will hereinafter be referred to as mouthwash "L".

In the series of tests, subjects were given a particular food containing a high amount of seasoning hereinafter to referred to as the insult. Shortly after receiving the insult, the subjects rinsed with either the A mouthwash or the L mouthwash whereupon their breath was olafactorally evaluated by a panel of judges on a blind basis at various times after treatment. Degree of "mal odor" was scored on the basis of a 4 point scale with a score of 0 indicating no mal odor and a score of 3 indicating high mal odor. On a succeeding day, subjects repeated the procedure but crossed over to the opposite rinse. At the end of the second day, scores were totaled and statistically treated to determine difference in performance.

The above procedure was tried with various insults as follows:

A. Insult: about 1.2 grams of concentrated garlic powder consumed by each subject in a shrimp scampi.

The results of the test of this insult were as follows:

| Mouthwash | Value of Initial Insult | Mean Values After Treatment Plus | | | | |
|---|---|---|---|---|---|---|
| | | 0 hr. | 1 hr. | 2 hr. | 3 hr. | 4 hr. |
| 6 A | 2.69 | 0.27 | 1.33 | 1.80 | 2.39 | 2.35 |
| L | 2.63 | 0.24 | 1.49 | 2.00 | 2.67 | 2.51 |
| Significance Level | | | 75% | 90% | 95% | 75% |

As can be seen from these values, the mouthwash of the instant invention provided significant reduction of mal odor due to the ingestion of the garlic at both 2 and 3 hours after treatment with directional superiority being shown for the period of 1 to 4 hours after treatment. Overall significance for this period was 90%.

B. INSULT: about 1.2 grams of concentrated garlic powder by each subject by ingestion of the powder on two slices of pizza.

The results of the test of this insult were as follows:

| Mouthwash | Value of Initial Insult | Mean Values After Treatment Plus | | | |
|---|---|---|---|---|---|
| | | 0 hr. | ½ hr. | 1 hr. | 2 hr. |
| 6 A | 2.64 | 0.14 | 0.65 | 0.94 | 1.13 |
| L | 2.67 | 0.03 | 0.79 | 0.93 | 1.59 |
| Significance Level | | | | | 95% |

As can be seen from these values that mouthwash of the instant invention provided superior reduction of mal odor due to the ingestion of the garlic and was significantly superior at the point of time 2 hours after treatment.

C. Insult: about 1.2 grams of concentrated garlic powder by each subject by ingesting a meal of ravioli containing the garlic.

The results of this test were as follows:

| Mouthwash | Value of Initial Insult | Mean Values After Treatment Plus | | | | |
|---|---|---|---|---|---|---|
| | | 0 hr. | ½ hr. | 1 hr. | 2 hr. | 4 hr. |
| 6A | 2.33 | 0.02 | 0.41 | 0.80 | 0.91 | 1.02 |
| L | 2.65 | 0.18 | 0.48 | 0.98 | 1.20 | 1.26 |

As can be seen from these values, the mouthwash of the instant invention provided superior reduction of mal odor due to the ingestion of the garlic.

EXAMPLE 10

Mouthwash 6A of Example 6 was screened in the test procedure outlined in Example 9 verses mouthwash L of Example E for effectiveness against morning mouth plus controlled breakfast insult. Each subject consumed:

1 5 ounce glass orange juice
2 scrambled eggs
4 slices bacon
1 slice toast
1 cup coffee and was requested to refrain from any oral hygiene on the morning of the test. Product allocation to panelists was based on the ranking of the initial scores according to intensity with the reverse treatment on the second day of the test. Three judges assessed strong mouth odor, i.e. intrinsic mal odor in combination with the above breakfast, using the following scale:

0 -No strong mouth odor
1 Slight strong mouth odor (maybe yes, maybe no)
2 - Definite strong mouth odor (just distinguishable)
3 -Intense strong mouth odor (bad, but could be worse)
4 Very intense strong mouth odor (as bad as you can get)

Odor assessments were obtained immediately following food intake, immediately after treatment, and one, two, and three hours post treatment.

The results of this test were as follows:

| Mouthwash | Initial Value of Insult | Mean Value After Treatment Plus | | | |
|---|---|---|---|---|---|
| | | 0 hr. | 1 hr. | 2 hr. | 3 hr. |
| A | 1.76 | 0.20 | 1.58 | 1.74 | 1.83 |
| L | 1.64 | 0.34 | 1.55 | 2.27 | 2.24 |
| Significance Level | | | | 95% | 95% |

As can be seen from the above results, the mouthwash of the instant invention provides significantly superior extended protection.

EXAMPLES 11 to 30

The following represent mouthwash formulations according to the instant invention.

(1) Polyoxyethylene 20 sorbitan monolaurate
(2) Polyoxyethylene 10 stearyl ether
(3) Polyoxyethylene 20 stearyl ether

| INGREDIENT | EXAMPLE 11 | | EXAMPLE 12 | | EXAMPLE 13 | | EXAMPLE 14 | |
|---|---|---|---|---|---|---|---|---|
| Essential Oil | | 0.25 | | 0.25 | | 0.20 | | 0.30 |
| Anionic surfactant | | | | | | | | |
|   Ratio of $C_{12}:C_{14}$ | 2.5/1 | | 2.5/1 | | 2.5/1 | | 2.5/1 | |
|   Cation | Na | | Na | | Na | | Na | |
|   Amount | | 0.30 | | 0.30 | | 0.30 | | 0.60 |
| Nonionic emulsifier | | | | | | | | |
|   Identity | (1) | | (2) | | (1) | | (1) | |
|   Amount | | 0.10 | | 0.25 | | 0.25 | | 0.25 |
| Ethanol | | 12.5 | | 12.5 | | 10.0 | | 10.0 |
| Humectant | | | | | | | | |
|   Identity | Sorbitol, 70% | | Sorbitol, 70% | | Glycerine | | Sorbitol, 70% | |
|   Amount | | 12.0 | | 12.0 | | 10.0 | | 12.0 |
| Alkali metal halide | | | | | | | | |
|   Identity | NaCl | | NaCl | | — | | NaCl | |
|   Amount | | 0.05 | | 0.05 | | 0 | | 0.03 |
| Sweetening agent | | | | | | | | |
|   Identity | Saccharin, sodium | | Saccharin, Sodium | | Saccharin, sodium | | Saccharin, sodium | |
|   Amount | | 0.05 | | 0.05 | | 0.02 | | 0.05 |
| Buffering salts | | | | | | | | |
|   Identity | $CH_3CO_2Na/CH_3CO_2H$ | | $CH_3CO_2Na/CH_3CO_2H$ | | — | | Na citrate/citric acid | |
|   Amount | | 0.05 | | 0.05 | | 0 | | 0.06 |
| Water | | to 100 | | to 100 | | to 100 | | to 100 |

| INGREDIENT | EXAMPLE 15 | | EXAMPLE 16 | | EXAMPLE 17 | | EXAMPLE 18 | |
|---|---|---|---|---|---|---|---|---|
| Essential Oil | | 0.4 | | 0.20 | | 0.30 | | 0.50 |
| Anionic surfactant | | | | | | | | |
|   Ratio of $C_{12}:C_{14}$ | 2.5/1 | | 2.5/1 | | 2.5/1 | | 4/1 | |
|   Cation | Na | | Na | | Mg | | Na | |
|   Amount | | 0.60 | | 0.30 | | 0.40 | | 0.30 |
| Nonionic emulsifier | | | | | | | | |
|   Identity | (1) | | (3) | | (1) | | (1) | |
|   Amount | | 0.25 | | 0.20 | | 0.20 | | 0.10 |
| Ethanol | | 10.0 | | 10.0 | | 10.0 | | 15.0 |
| Humectant | | | | | | | | |
|   Identity | Glycerine Sorbitol, 70% | 5.0 5.0 | Sorbitol, 70% | | Glyercine | | Sorbitol, 70% | |

-continued

| | | | | |
|---|---|---|---|---|
| Amount | | 12.0 | 10.0 | 10.0 |
| Alkali metal halide | | | | |
| Identity | NaCl | NaCl | — | NaCl |
| Amount | 0.03 | 0.05 | 0 | 0.05 |
| Sweetening agent | | | | |
| Identity | Saccharin, sodium | Saccharin, sodium | Saccharin, sodium | Saccharin, sodium |
| Amount | 0.05 0.05 | 0.05 | 0.04 | 0.10 |
| Buffereing salts | | | | |
| Identity | CH$_3$CO$_2$Na/ CH$_3$CO$_2$H | CH$_3$CO$_2$Na/ CH$_3$CO$_2$H | Na citrate/ citric acid | — |
| Amount | 0.05 | 0.04 | 0.06 | 0 |
| Water | to 100 | to 100 | to 100 | to 100 |

| INGREDIENTS | EXAMPLE 19 | EXAMPLE 20 | EXAMPLE 21 | EXAMPLE 22 |
|---|---|---|---|---|
| Essential Oil | 0.30 | 0.30 | 0.25 | 0.25 |
| Anionic surfactant | | | | |
| Ratio of C$_{12}$:C$_{14}$ | 4/1 | 1/1 | 2.5/1 | 50/1 |
| Cation | Mg | Na | Na | Na |
| Amount | 0.50 | 0.50 | 0.60 | 0.50 |
| Nonionic emulsifier | | | | |
| Identity | (1) | (1) | — | — |
| Amount | 0.20 | 0.30 | 0 | 0 |
| Ethanol | 15.0 | 12.5 | 15.0 | 10.0 |
| Humectant | | | | |
| Identity | Glycerine | Glycerine | Sorbitol, 70% | Sorbitol, 70% |
| Amount | 10.0 | 10.0 | 12.5 | 12.5 |
| Alkali metal halide | | | | |
| Identity | — | NaCl | — | — |
| Amount | 0 | 0.05 | 0 | 0 |
| Sweetening agent | | | | |
| Identity | — | Saccharin, | Saccharin, | Saccharin, |
| Amount | 0 | 0.05 | 0.07 | 0.07 |
| Buffereing salts | | | | |
| Identity | CH$_3$CO$_2$Na/ CH$_3$CO$_2$H | CH$_3$CO$_2$Na/ CH$_3$CO$_2$H | — | — |
| Amount | 0.05 | 0.05 | 0 | 0 |
| Water | to 100 | to 100 | to 100 | to 100 |

| INGREDIENTS | EXAMPLE 23 | EXAMPLE 24 | EXAMPLE 25 | EXAMPLE 26 |
|---|---|---|---|---|
| Essential Oil | 0.25 | 0.50 | 0.25 | 0.25 |
| Anionic surfactant | | | | |
| Ratio of C$_{12}$:C$_{14}$ | 50/1 | 2.5/1 | 1:1 | 1:1 |
| Cation | Na | Na | Na | Na |
| Amount | 0.60 | 0.60 | 0.20 of each (total 0.40) | 0.20 of each (total 0.40) |
| Nonionic emulsifier | | | | |
| Identity | (1) | (1) | (1) | — |
| Amount | 0.20 | 0.20 | 0.25 | 0 |
| Ethanol | 10.0 | 20.0 | 12.0 | 12.0 |
| Humectant | | | | |
| Identity | Sorbitol, 70% | Glycerine | Sorbitol, 70% | Sorbitol, 70% |
| Amount | 12.5 | 10.0 | 12.0 | 12.0 |
| Alkali metal halide | | | | |
| Identity | — | NaCl | NaCl | NaCl |
| Amount | 0 | 0.05 | 0.05 | 0.05 |
| Sweetening agent | | | | |
| Identity | Saccharin, sodium | Saccharin, sodium | Saccharin, sodium | Saccharin, sodium |
| Amount | 0.07 | 0.02 | 0.07 | 0.07 |
| Buffering salts | | | | |
| Identity | — | Na citrate/ citric acid | CH$_3$CO$_2$Na/ CH$_3$CO$_2$H | CH$_3$CO$_2$Na/ CH$_3$CO$_2$H |
| Amount | 0 | 0.10 | 0.05 | 0.05 |
| Water | to 100 | to 100 | to 100 | to 100 |

| INGREDIENTS | EXAMPLE 27 | EXAMPLE 28 | EXAMPLE 29 | EXAMPLE 30 |
|---|---|---|---|---|
| Essential Oil | 0.25 | 0.30 | 0.10 | 0.25 |
| Anionic surfactant | | | | |
| Ratio C$_{12}$:C$_{14}$ | 2.5/1 | 2.5/1 | 4/1 | 75/1 |
| Cation | NH$_4$ | Na | Mg | Na |
| Amount | 0.30 | 0.30 | 0.30 | 0.30 |
| Nonionic emulsifier | | | | |
| Identity | (1) | (1) | — | (1) |
| Amount | 0.25 | 0.25 | 0 | 0.25 |
| Ethanol | 12.0 | 12.0 | 15.0 | 11.9 |
| Humectant | | | | |
| Identity | Glycerine | Corn syrup | Glycerine | Sorbitol, 70% |
| Amount | 10.0 | 25.0 | 10.0 | 12.0 |
| Alkali metal halide | | | | |
| Identity | — | NaCl | — | NaCl |

| | | | | |
|---|---|---|---|---|
| Amount | 0 | 0.05 | 0 | 0.05 |
| Sweetening agent | | | | |
| Identity | Saccharin, sodium | — | Saccharin, sodium | Saccharin, sodium |
| Amount | 0.02 | 0 | 0.02 | 0.07 |
| Buffering salts | | | | |
| Identity | $NaH_2PO_4$/ $Na_2HPO_4$ | $CH_3CO_2Na$/ $CH_3CO_2H$ | — | $CH_3CO_2Na$/ $CH_3CO_2H$ |
| Amount | 0.05 | 0.05 | 0 | 0.05 |
| Water | to 100 | to 100 | to 100 | to 100 |

What is claimed is:

1. A stable liquid, physiologically acceptable, germicide free, antibacterial mouthwash, comprising:
   (a) about 5 to about 15 percent, by weight of said mouthwash, of ethanol;
   (b) about 0.1 to about 2-percent, by weight of said mouthwash, of an essential oil flavor mixture selected from the group consisting of spearmint, peppermint and mixtures thereof;
   (c) about 0.1 to about 0.6 percent, by weight of said mouthwash, of an alkyl sulfate anionic surfactant mixture wherein:
      (i) said mixture consists essentially of a dodecyl sulfate salt and a tetradecyl sulfate salt wherein the cationic moiety of said salts is selected from the group consisting of sodium, potassium, magnesium, ammonium, and substituted ammonium ions and mixtures thereof, and
      (ii) wherein said dodecyl sulfate is present in said mixture in a weight ratio to said tetradecyl sulfate of about 4:1 to about 1:1;
   (d) 0 to about 3 percent, by weight of said mouthwash, of a nonionic emulsifier;
   (e) 0 to about 25 percent, by weight of said mouthwash, of a humectant;
   (f) 0 to about 2percent, by weight of said mouthwash, of an alkali metal halide; ;
   (g) 0 to about 1 percent, by weight of said mouthwash, of a buffering salt pair, wherein said salt pair is capable of buffering said mouthwash to a pH of between about 3 and about 8;
   (h) 0 to about 2 percent, by weight of said mouthwash, of sodium saccharin, or an amount sufficient to provide a sweetening effect equivalent thereto of a sweetening agent; and
   (i) water.

2. A mouthwash according to claim 1, wherein:
   (a) said nonionic emuslifier is present at a level of at least about 0.1 percent;
   (b) said humecant is present at a level of at least about 5 percent; and
   (c) said mouthwash contains at least about 0.01 percent sodium saccharin, or an amount sufficient to provide a sweetening effect equivalent therto of a sweetening agent.

3. A mouthwash according to claim 1, wherein:
   (a) said ethanol is present at a level of about 10 to about 15 percent;
   (b) said flavor mixture is present at a level of about 0.1 to about 0.75 percent;
   (c) said anionic surfactant mixture is present at a level of about 0.1 to about 0.4 percent;
   (d) said nonionic emulsifier is present at a level of about 0.1 to about 0.5 percent;
   (e) said humecant is present at a level of about 5 to about 20 percent; and
   (f) said mouthwash contains about 0.01 to about 0.5 percent of sodium saccharin, or an amount sufficient to provide a sweetening effect equivalent thereto of a sweetening agent.

4. A mouthwash according to claim 1 wherein said dodecyl sulfate salt is sodium dodecyl sulfate and said tetradecyl sulfate salt is sodium tetradecyl sulfate.

5. A mouthwash according to claim 1 wherein said nonionic emulsifier is selected from the group consisting of:
   (a) polyoxyethylene 20 sorbitan monolaurate;
   (b) polyoxyethylene 20 stearyl ether;
   (c) polyoxyethylene 20 isohexadecyl ether;
   (d) polyoxyethylene 100 stearate;
   (e) polyoxyethylene 10 stearyl ether; and mixtures thereof.

6. A mouthwash according to claim 1 wherein said ratio of said dodecyl sulfate to said tetradecyl sulfate is about 4:1 to about 2:1.

7. A mouthwash according to claim 1 wherein said ratio of said dodecyl sulfate to said tetradecyl sulfate is about 4:1 to about 3:1.

8. A mouthwash according to claim 3 wherein:
   (a) said dodecyl sulfate is sodium dodecyl sulfate and said tetradecyl sulfate salt is sodium tetradecyl sulfate;
   (b) said nonionic emulsifier is selected from the group consisting of:
      (i) polyoxyethylene 20 sorbitan monolaurate,
      (ii) polyoxyethylene 20 stearyl ether,
      (iii) polyoxyethylene 20 isohexadecyl ether,
      (iv) polyoxyethylene 100 stearate,
      (v) polyoxyethylene 10 stearyl ether, and mixtures thereof; and
   (c) said ratio of said dodecyl sulfate to said tetradecyl sulfate is about 4:1 to about 2:1.

9. A mouthwash according to claim 8 wherein:
   (a) said ethanol is present at a level of about 12 to about 13 percent;
   (b) said flavor mixture is present at a level of about 0.2 to about 0.5 percent;
   (c) said anionic surfactant mixture is present at a level of about 0.2 to about 0.4 percent;
   (d) said nonionic emulsifier is present at a level of about 0.2 to about 0.4 percent;
   (e) said humectant is present at a level of about 10 to about 15 percent; and
   (f) said mouthwash contains about 0.05 to about 0.075 percent of sodium saccharin, or an amount sufficient to provide a sweetening effect equivalent thereto of a sweetening agent.

10. A mouthwash according to claim 9, wherein:
   (a) said nonionic emulsifier is polyoxyethylene 20 sorbitan monolaurate;
   (b) said alkali metal halide is sodium chloride and wherein said sodium chloride is present at a level of about 0.01 to about 0.1 percent; and (c) said buffering salt pair is sodium acetate and acetic acid wherein the ratio of said sodium acetate to said acetic acid is about 3 to 2 and further wherein said pair is present in said mouthwash at a level of about 0.01 to about 0.1 percent.

11. A stable liquid, physiologically acceptable, germicide free, antibacterial mouthwash consisting essentially of:
(a) about 10 to about 15 percent, by weight of said mouthwash, of ethanol;
(b) about 0.2 to about 0.5 percent, by weight of said mouthwash, of an essential oil flavor mixture selected from the group consisting of spearmint, peppermint and mixtures thereof;
(c) about 0.2 to about 0.4 percent, by weight of said mouthwash of a mixture of sodium dodecyl sulfate and sodium tetradecyl sulfate wherein the ratio of said sodium dodecyl sulfate to said sodium tetradecyl sulfate is about 4:1 to about 2:1;
(d) about 0.2 to about 0.4 percent, by weight of said mouthwash, of polyoxyethylene 20 sorbitan monolaurate;
(e) about 10 to about 15 percent, by weight of said mouthwash, of a humectant;
(f) about 0.05 to about 0.075 percent by weight of said mouthwash, of sodium saccharin, or an amount sufficient to provide a sweetening effect equivalent thereto of a sweetening agent;
(g) about 0.01 to about 0.1 percent, by weight of said mouthwash, of sodium chloride;
(h) about 0.01 to about 0.1 percent, by weight of said mouthwash of a mixture of sodium acetate and acetic acid wherein the ratio of said sodium acetate to said acetic acid is about 3:2; and
(i) water.

12. A stable liquid, physiologically acceptable, germicide free, antibacterial mouthwash consisting essentially of:
(a) about 12 and ½ percent by weight of said mouthwash ethanol;
(b) about ¼ percent by weight of said mouthwash of an essential oil flavor mixture selected from the group consisting of spearmint, peppermint and mixtures thereof;
(c) about 3/10 percent by weight of said mouthwash of a mixture of sodium dodecyl sulfate and sodium tetradecyl sulfate wherein the ratio of said sodium dodecyl sulfate to said sodium tetradecyl sulfate is about 3:1 to about 2:1;
(d) about ¼ percent by weight of said mouthwash of polyoxyethylene 20 sorbitan monolaurate;
(e) about 12 percent by weight of said mouthwash of sorbitol;
(f) about 5/100 percent by weight of said mouthwash of sodium chloride;
(g) about 5/100 percent by weight of said mouthwash of sodium saccharin; and
(h) about 5/100 percent by weight of a mixture of sodium acetate and acetic acid wherein the ratio of said sodium acetate to said acetic acid is about 3:2; and
(i) water.

13. a physiologically acceptable method of reducing bacteria in the mouth comprising contacting the tissue of the oral cavity with the mouthwash according to claim 1.

14. A physiologically acceptable method of reducing bacteria in the mouth comprising contacting, for a time sufficient to reduce said baceria, the tissue of the oral cavity with the mouthwash according to claim 1.

15. A physiologically acceptable method of reducing bacteria in the mouth comprising contacting, for a time sufficient to reduce said bacteria, the tissue of the oral cavity with the mouthwash according to claim 3.

16. A physiologically acceptable method of reducing bacteria in the mouth comprising contacting, for a time sufficient to reduce said bacteria, the tissue of the oral cavity with the mouthwash according to claim 8.

17. A physiologically acceptable method of reducing bacteria in the mouth comprising contacting, for a time sufficient to reduce said bacteria, the tissue of the oral cavity with the mouthwash according to claim 9.

18. A physiologically acceptable method of reducing bacteria in the mouth comprising contacting, for a time sufficient to reduce said bacteria, the tissue of the oral cavity with the mouthwash according to claim 10.

19. A physiologically acceptable method of reducing bacteria in the mouth comprising contacting, for a time sufficient to reduce said bacteria, the tissue of the oral cavity with the mouthwash according to claim 11.

20. A physiologically acceptable method of reducing bacteria in the mouth comprising contacting, for a time sufficient to reduce said bacteria, the tissue of the oral cavity with the mouthwash according to claim 12.

21. A method of reducing mal odor in the mouth associated with the ingestion of foods containing at least one food flavorant selected from the group consisting of onion and garlic comprising contacting the tissue of the oral cavity, for a time to reduce said mal odor, with the mouthwash according to claim 1.

22. A method of reducing mal odor in the mouth associated with the ingestion of foods containing at least one food flavorant selected from the group consisting of onion and garlic comprising contacting the tissue of the oral cavity, for a time to reduce said mal odor, with the moutwash according to claim 3.

23. A method of reducing mal odor in the mouth associated with the injestion of foods containing at least one food flavorant selected from the group consisting of onion and garlic comprising contacting the tissue of the oral cavity, for a time reduce said mal odor, with the mouthwash according to claim 8.

24. A method of reducing mal odor in the mouth associated with the ingestion of foods containing at least one food flavorant selected from the group consisting of onion and garlic comprising contacting the tissue of the oral cavity, for a time to reduce said mal odor, with the mouthwash according to claim 9.

25. A method of reducing mal odor in the mouth associated with the ingestion of foods containing at least one food flavorant selected from the group consisting of onion and garlic comprising contacting the tissue of the oral cavity, for a time to reduce said mal odor, with the mouthwash according to claim 10.

26. A method of reducing mal odor in the mouth associated with the ingestion of foods containing at least one food flavorant selected from the group consisting of onion and garlic comprising contacting the tissue of the oral cavity, for a time to reduce said mal odor, with the mouthwash according to claim 11.

27. A method of reducing mal odor in the mouth associated with the ingestion of foods containing at least one food flavorant selected from the group consisting of onion and garlic comprising contacting the tissue of the oral cavity, for a time to reduce said mal odor, with the mouthwash according to claim 12.

28. An antibacterial, germicide free, physiologically acceptable doublemint flavored mouthwash comprising:
   (a) 45 to about 60 percent by weight of said mouthwash of water;
   (b) less than about 20 percent by weight of said mouthwash of ethanol;
   (c) about 0.1 to about 2 percent by weight of an essential oil flavor mixture selected from the group consisting of spearmint, peppermint and mixtures thereof;
   (d) about 0.1 to about 0.6 percent by weight of said mouthwash, of an alkyl sulfate anionic surfactant mixture wherein:
      (i) said mixture consists essentially of dodecyl sulfate salt and a tetradecyl sulfate salt wherein the cationic moiety of said salts is selected from the group consisting of sodium, potassium, magnesium, ammonium, substituted ammonium and morpholenium ions and mixtures thereof, and
      (ii) said dodecyl sulfte is present in said mixture in a weight ratio to said tetradecyl sulfate of about 75:1 to about 1:1;
   (e) 0 to about 3 percent, by weight of said mouthwash, of a nonionic emulsifier;
   (f) 0 to about 25 percent, by weight of said mouthwash, of a humectant;
   (g) 0 to about 2 percent, by weight of said mouthwash, of an alkali metal halide;
   (h) 0 to about 1 percent, by weight of said mouthwash, of a buffering salt pair, wherein said salt pair is capable of buffering said mouthwash to a pH of between about 3 and about 8; and
   (i) 0 to about 2 percent, by weight of said mouthwash, of sodium saccharin, or an amount sufficient to provide a sweetening effect equivalent thereto of a sweetening agent.

29. A mouthwash according to claim 28 wherein:
   (a) said nonionic emulsifier is present at a level of at least about 0.1 percent;
   (b) said humectant is present at a level of at least about 5 percent; and
   (c) said mouthwash contains at least about 0.01 percent sodium saccharin or an amount sufficient to provide a sweetening effect equivalent thereto of a sweetening agent.

30. A mouthwash according to claim 28, wherein:
   (a) said ethanol is present at a level of about 10 to about 15 percent;
   (b) said flavor mixture is present at a level of about 0.1 to about 0.75 percent;
   (c) said anionic surfactant mixture is present at a level of about 0.1 to about 0.4 percent, and wherein the the ratio of dodecyl sulfate to tetradecyl sulfate is about 4:1 to about 1:1;
   (d) said nonionic emulsifier is present at a level of about 0.1 to about 0.5 percent;
   (e) said humectant is present at a level of about 5 to about 20 percent; and
   (f) said mouthwash contains about 0.01 to about 0.5 percent of sodium saccharin, or an amount sufficient to provide a sweetening effect equivalent thereto of a sweetening agent.

31. A mouthwash according to claim 28 wherein said dodecyl sulfate salt is sodium dodecyl sulfate and said tetradecyl sulfate salt is sodium tetradecyl sulfate.

32. A mouthwash according to claim 28 wherein said nonionic emulsifier is selected from the group consisting of:
   (a) polyoxyethylene 20 sorbitan monolaurate;
   (b) polyoxyethylene 20 stearyl ether;
   (c) polyoxyethylene 20 isohexadecyl ether;
   (d) polyoxyethylene 100 stearate;
   (e) polyoxyethylene 10 stearyl ether; and mixtures thereof.

33. A mouthwash according to claim 29 wherein said ratio of said dodecyl sulfate to said tetradecyl sulfate is about 4:1 to about 2:1.

34. A mouthwash according to claim 28 wherein said ratio of said dodecyl sulfate to said tetradecyl sulfate is about 4:1 to about 3:1.

35. A mouthwash according to claim 30 wherein:
   (a) said dodecyl sulfate is sodium dodecyl sulfate and said tetradecyl sulfate salt is sodium tetradecyl sulfate;
   (b) said nonionic emulsifier is selected from the group consisting of:
      (i) polyoxyethylene 20 sorbitan monolaurate,
      (ii) polyoxyethylene 20 stearyl ether,
      (iii) polyoxyethylene 20 isohexadecyl ether,
      (iv) polyoxyethylene 100 stearate,
      (v) polyoxyethylene 10 stearyl ether, and mixtures thereof; and
   (c) said ratio of said dodecyl sulfate to said tetradecyl sulfate is about 4:1 to about 2:1.

36. A mouthwash according to claim 35 wherein:
   (a) said ethanol is present at a level of about 12 to about 13 percent;
   (b) said flavor mixture is present at a level of about 0.2 to about 0.5 percent;
   (c) said anionic surfactant mixture is present at a level of about 0.2 to about 0.4 percent;
   (d) said nonionic emulsifier is present at a level of about 0.2 to about 0.4 percent;
   (e) said humectant is present at a level of about 10 to about 15 percent; and
   (f) said mouthwash contains about 0.05 to about 0.075 percent of sodium saccharin, or an amount sufficinet to provide a sweetening effect equivalent thereto of a sweetening agent.

37. A mouthwash according to claim 36, wherein:
   (a) said nonionic emulsifier is polyoxyethylene 20 sorbitan monolaurate;
   (b) said alkali metal halide is sodium chloride and wherein said sodium chloride is present at a level of about 0.01 to about 0.1 percent; and
   (c) said buffering salt pair is sodium acetate and acetic acid wherein the ratio of said sodium acetate to said acetic acid is about 3 to 2 and further wherein said pair is present in said mouthwash at a level of about 0.01 to about 0.1 percent.

38. An antibacterial, germicide free, physiologically acceptable doublemint flavored mouthwash consisting essentially of:
   (a) 45 to about 90 percent by weight of said mouthwash of water;
   (b) about 10 to about 15 percent, by weight of said mouthwash, of ethanol;
   (c) about 0.2 to about 0.5 percent, by weight of said mouthwash, of an essential oil flavor mixture selected from the group consisting of spearmint, pepperment and mixtures thereof;
   (d) about 0.2 to about 0.4 percent, by weight of said mouthwash of a mixture of sodium dodecyl sulfate and sodium tetradecyl sulfate wherein the ratio of said sodium tetradecyl sulfate wherein the ratio of said sodium dodecyl sulfate to said sodium tetradecyl sulfate is about 75:1 to about 2:1;
(e) about 0.2 to about 0.4 percent, by weight of said mouthwash, of polyoxyethylene 20 sorbitan monolaurate;
(f) about 10 to about 15 percent, by weight of said mouthwash, of a humectant;
(g) about 0.05 to about 0.075 percent by weight of said mouthwash, of sodium saccharin, or an amount sufficient to provide a sweetening effect equivalent thereto of a synthetic sweetening agent;
(h) about 0.01 to about 0.1 percent, by weight of said mouthwash of sodium chloride; and
(i) about 0.01 to about 0.1 percent, by weight of said mouthwash of a mixture of sodium acetate and acetic said wherein the ratio of said sodium acetate to said acetic acid is about 3:1.

39. An antibacterial, germicide free, physiologically acceptable doublemint flavored mouthwash comprising:
(a) 45 to about 90 percent by weight of said mouthwash of water;
(b) abut 12 and ½ percent by weight of said mouthwash of ethanol;
(c) about ¼ percent by weight of said mouthwash of an essential oil flavor mixture selected from the group consisting of spearmint, peppermint and mixtures thereof;
(d) about 3/10 percent by weight of said mouthwash of a mixture of sodium dodecyl sulfate and sodium tetradecyl sulfate wherein the ratio of said sodium dodecyl sulfate to said sodium tetradecyl sulfate is about 3:1 to about 2:1,
(e) about 174 percent by weight of said mouthwash of polyoxyethylene 20 sorbitan monolaurate;
(f) about 12 percent by weight of said mouthwash of sorbitol;
(g) about 5/100 percent by weight of said mouthwash of sodium chloride;
(h) about 5/100 percent by weight of said mouthwash of sodium saccharin; and
(i) about 5/100 percent, by weight of said mouthwash of a mixture of sodium acetate and acetic acid wherein the ratio of said sodium acetate to said acetic acid is about 3:1.

40. A physiologically acceptable method of reducing bacteria in the mouth comprising contacting the tissue of the oral cavity with the mouthwash according to claim 28.

41. A physiologically acceptable method of reducing bacterial in the mouth comprising contacting, for a time sufficient to reduce said bacteria, the tissue of the oral cavity with the mouthwash according to claim 28.

42. A physiologically acceptable method of reducing bacteria in the mouth comprising contacting, for a time sufficient to reduce said bacteria, the tissue of the oral cavity with the mouthwash according to claim 30.

43. A physiologically acceptable method of reducing baceteria in the mouth comprising contacting, for a time sufficient to reduce said bactria, the tissue of the oral cavity with the mouthwash according to claim 35.

44. A physiologically acceptable method of reducing bacteria in the mouth comprising contacting, for a time sufficient to reduce said bacteria, the tissue of the oral cavity with the mouthwash according to claim 36.

45. A physiologically acceptable method of reducing bacteria in the mouth comprising contacting, for a time sufficient to reduce said bacteria, the tissue of the oral cavity with the mouthwash according to claim 37.

46. A physiologically acceptable method of reducing bacteria in the mouth comprising contacting, for a time sufficient to reduce said bacteria, the tissue of the oral cavity with the mouthwash according to claim 38.

47. A physiologically acceptable method of reducing bacteria in the mouth comprising contacting, for a time sufficient to reduce said bacteria, the tissue of the oral cavity with the mouthwash according to claim 39.

48. A method of reducing mal odor in the mouth associated with the ingestion of foods containing at least one food flavorant selected from the group consisting of onion and garlic comprising contcting the tissue of the oral cavity, for a time to reduce said mal odor, with the mouthwash according to claim 28.

49. A method of reducing mal odor in the mouth associated with the ingestion of foods containing at least one food flavorant selected from the group consisting of onion and garlic comprising contacting the tissue of the oral cavity, for a time to reduce said mal odor, with the mouthwash according to claim 30.

50. A method of reducing mal odor in the mouth associated with the ingestion of foods containing at least one food flavorant selected from the group consisting of onion and garlic comprising contacting the tissue of the oral cavity, for a time to reduce said mal odor, with the mouthwash according to claim 35.

51. A method of reducing mal odor in the mouth associated with the ingestion of foods containing at least one food flavorant selected from the group consisting of onion and garlic comprising contacting the tissue of the oral cavity, for a time to reduce said mal odor, with the mouthwash according to claim 36.

52. A method of reducing mal odor in the mouth associated with the ingestion of foods containing at least one food flavorant selected from the group consisting of onion and garlic comprising contacting the tissue of the oral cavity, for a time to reduce said mal odor, with the mouthwash according to claim 37.

53. A method of reducing mal odor in the mouth associated with the ingestion of foods containing at least one food flavorant selected from the group consisting of onion and garlic comprising contacting the tissue of the oral cavity, for a time to reduce said mal odor, with the mouthwash according to claim 38.

54. A method of reducing mal odor in the mouth associated with the ingestion of foods containing at least one food flavorant selected from the group consisting of onion and garlic comprising contacting the tissue of the oral cavity, for a time to reduce said mal odor, with the mouthwash according to claim 39.

* * * * *